United States Patent [19]
Ng

[11] Patent Number: 5,949,899
[45] Date of Patent: Sep. 7, 1999

[54] APPARATUS FOR MEASURING AND ANALYZING ELECTROPHORESIS IMAGES

[75] Inventor: David Ng, Toronto, Canada

[73] Assignee: Nebular Vision Research & Development Inc., Toronto

[21] Appl. No.: 08/724,467

[22] Filed: Oct. 1, 1996

[51] Int. Cl.[6] ................................................ G06K 9/00
[52] U.S. Cl. .................... 382/129; 364/528.01; 204/608; 204/612; 204/457
[58] Field of Search .................................. 382/128, 129, 382/286, 132, 133; 348/135, 137, 61, 142; 356/129, 497; 364/528.01; 214/618, 612

[56] References Cited

U.S. PATENT DOCUMENTS

| | | |
|---|---|---|
| 3,833,796 | 9/1974 | Fetner et al. . |
| 4,592,089 | 5/1986 | Hartman . |
| 4,706,192 | 11/1987 | Nasu et al. . |
| 4,771,384 | 9/1988 | Daniels et al. . |
| 4,810,348 | 3/1989 | Sarrine et al. ........................... 204/299 |
| 4,928,169 | 5/1990 | Leberl et al. ............................. 358/93 |
| 4,970,672 | 11/1990 | Snodgrass . |
| 5,371,671 | 12/1994 | Anderson et al. . |
| 5,917,602 | 3/1998 | Kenning ................................... 364/500 |

Primary Examiner—Andrew W. Johns
Assistant Examiner—Hiev C. Le
Attorney, Agent, or Firm—Bereskin & Parr

[57] ABSTRACT

A system for measuring and analyzing an image of a gel electrophoresis, includes measuring apparatus and a processor. The measuring apparatus includes a frame mountable in a fixed location relative to the image, including a bar extending along a first axis, a carriage coupled to the bar and slidable along the first axis, an alignment device extending transversely from the carriage along a second axis for aligning selected components of the image, and a distance sensor operatively coupled to the carriage for sensing the distance travelling by the carriage and generating distance signals. The processor is operatively coupled to the measuring apparatus and processes the distance signals and generates maps based thereon. The subject system is well suited for constructing restriction enzyme maps for an image of bands created by subjecting DNA to gel electrophoresis.

11 Claims, 5 Drawing Sheets

APPARATUS FOR MEASURING AND ANALYZING ELECTROPHORESIS IMAGES

FIELD OF THE INVENTION

The present invention relates to apparatus for measuring and analyzing images created by subjecting biological material to electrophoresis and, more particularly, to systems for constructing DNA restriction enzyme maps.

BACKGROUND OF THE INVENTION

Heritable information in biological systems is stored in macromolecules of deoxyribonucleic acid (DNA) or ribonucleic acid (RNA). These molecules are polymers made up of four different base residues. Each base is attached to a sugar (deoxyribose or ribose for DNA or RNA, respectively) and phosphate group which form the backbone of the molecule. Each base-sugar-phosphate unit is called a nucleotide. The sequence of these nucleotides determines the content of the biological information. Generally, this information is used to manufacture proteins (polypeptides), which in turn are made up of chains of amino acid residues.

Electrophoresis is a common technique for separating these molecules by size. At physiological pH, the proton from the phosphate group in the backbone of the nucleic acid dissociates, giving molecules of DNA and RNA a negative charge. Thus, when placed in a constant electric field and the appropriate buffer, they would migrate towards the cathode.

A heterogeneous sample of DNA or RNA consisting of molecules of various sizes, however, cannot be separated in a solution because of the homogeneity of the phosphate backbone. This gives strands of nucleic acids nearly identical charge-to-mass ratios, regardless of their lengths. As a result, all the strands in the sample would migrate towards the cathode at the same rate and no separation would occur.

Electrophoresis is commonly used in conjunction with a semisolid gel made of agarose (a polysaccharide extracted from seaweed), or of polyacrylamide (a synthetic polymer) under a constant electric field (i.e. standard gel electrophoresis). In both situations, the gel forms minute pores which act as a molecular sieve which the DNA or RNA molecules can migrate through. This permits the separation of these molecules on the basis of size. Essentially, smaller molecules will migrate quicker through the gel than larger molecules because they can work their way through the pores with greater ease. Larger molecules will have greater difficulty passing through the pores and thus will migrate towards the cathode at a slower rate. The pore size can be controlled by the investigator by changing the concentration of the agarose or acrylamide in the gel. This permits the investigator to resolve fragments of nucleic acid as large as 30,000 nucleotides on an agarose gel in a constant electric field. Nucleic acid fragments up to 500 nucleotides long and differing in only one nucleotide can be resolved using a polyacrylamide gel.

Pulsed-field gel electrophoresis (PFGE) is commonly used to separate large fragments of DNA (30,000 nucleotides to 10 million nucleotides) and is particularly useful for separating entire chromosomes. PFGE is similar to standard gel electrophoresis except the DNA sample is subjected to an electric field which originates from different angles. Short electronic pulses from various angles allow very large DNA fragments to work their way through the pores. PFGE permits very large DNA fragments to be sorted according to their lengths, with the smaller fragments migrating quicker towards the cathode than the larger fragments.

Gel electrophoresis can also be used to separate proteins according to length. Proteins, in their native form, fold into various conformations forming globular or cylindrical structures. Thus, to separate these molecules according to their length, they must be unfolded, or denatured. Protein denaturation can be accomplished by adding a strong detergent in the electrophoresis solution. The detergent is amphipathic, that is, one end of the molecule is hydrophobic, while the other end is hydrophillic (and carries a negative charge at neutral pH). In solution, the hydrophobic end of the detergent interacts with each amino acid while the hydrophillic end protrudes from the protein. The protein is forced into a linear conformation due to the repulsion by the hydrophillic ends of the detergent. Under these conditions, the denatured proteins will have a similar charge-to-mass ratio, much like nucleic acids. Therefore, the same principle used to separate nucleic acids can also be used to separate protein according to length. Proteins are typically separated using standard gel electrophoresis in a polyacrylamide gel.

To determine the length of unknown fragments of DNA, RNA, or protein, a standard is loaded into a well cast in the gel. The standard contains fragments of DNA, RNA, or protein with known lengths and is run simultaneously with the unknown samples loaded in separate wells. By measuring the distance each known fragment has migrated from the originating well, one can construct a best-fit curve and determine the length of each unknown fragment.

Restriction endonucleases have revolutionized molecular biology. These molecules are enzymes which cleave DNA at short, specific sequences in the DNA. They allow the investigator to cut large DNA fragments into smaller, more manageable fragments of DNA. Currently, there are several hundreds of restriction endonucleases which recognize and cleave different sequences. Because of their sequence recognition specificity, they serve as important landmarks when studying an unknown fragment of DNA. A map of these sites, also known as a restriction enzyme map, is fundamental when analyzing DNA. DNA fragments of the same length but containing different sequence may produce a different subset of DNA fragments when cut with one or more restriction endonucleases. When these fragments are fractionated by gel electrophoresis, a unique banding pattern may be observed. This banding pattern can serve as a molecular fingerprint which can be used to differentiate DNA of the same fragment length but are composed of different sequences.

Restriction enzyme maps are particularly important for DNA cloning, DNA mutagenesis, genetic mapping and engineering. They establish the "blueprint" for the DNA from which more detailed experimentation can take place.

Restriction enzyme maps can be constructed by several techniques and most rely on data obtained from gel electrophoresis. Two or more restriction enzyme sites can be mapped by "inspection", provided the restriction enzymes create a limited number of fragments (i.e. less than 7). Essentially, an investigator compares banding patterns obtained after complete digestion with one restriction endonuclease (enzyme A or B) with a sample of DNA completely digested with both restriction endonucleases together (enzyme A and B). From this data, the investigator can deduce plausible maps which fit the data.

An alternative approach is to digest a sample of DNA with a single restriction endonuclease such that each fragment of DNA is cut once by the enzyme, despite the presence of multiple recognition sequences. Such a digest is termed a partial DNA digestion. This reaction creates a population of fragments of varying sizes. When these fragments are viewed after gel electrophoresis, the banding pattern is essentially meaningless due to the numerous bands. However, when these DNA fragments are immobilized onto a positively charged membrane (such as nitrocellulose or nylon), all the desired fragments can be identified using a labelled probe which is complimentary in sequence to one of the terminis of the original DNA fragments by DNA hybridization. The fragments which contain a common terminus can be detected using autoradiography (X-ray film). By calculating the size difference between adjacent and consecutive bands, one can generate a map for that particular restriction endonuclease.

Hybridization is a powerful technique for detecting the presence of a sequence in nucleic acid. DNA and RNA are composed of four different base residues; cytosine, guanine, adenine, and thymine (or uracil, in the case of RNA). These bases follow pairing rules; adenine pairs with thymine (or uracil), while cytosine pairs with guanine. DNA and RNA strands are polar, that is, strands run from 5' to 3'. DNA, and in some cases, RNA, can be found as double stranded structures. These structures consist of oppositely oriented strands held together by base pairing (i.e. one strand runs 5' to 3', while its complimentary strand runs 3' to 5' with respect to the first strand). Thus, to detect a certain sequence in a sample of nucleic acid, one can generate a probe containing complimentary sequence which as been labelled. Under appropriate hybridization conditions, the probe will base pair with the targeted sequence. Thus, fragments containing the target sequence can be identified by hybridization.

In many situations, more than one plausible map may be possible from the data obtained from complete single and double digestions. Thus, it is possible the correct map may not have been deduced by the investigator. In addition, this approach becomes very tedious with each additional band created by the digestion because the number of possible combinations increases factorially. However, computers are particularly well suited for handling such tasks.

A collection of clones containing small fragments of genomic DNA, collectively representing the entire genome, is known as a genomic library. One can construct a high-resolution genomic map by mapping individual clones by partial digestion and assembling or ordering the clones based on their restriction enzyme maps (or "fingerprints"). For example, two clones containing DNA from the identical region of the genome will have the same fingerprint. If they were from completely different regions of the genome, they would likely have very distinct fingerprints. However, if the clones contain overlapping regions of DNA, they would share similarities in their maps. In the latter situation, overlapping clones can be assembled together to construct a contig (a composite map). Eventually, multiple contigs can be assembled into a map representing the entire genome.

Mapping entire genomes by partial digestion has become a relatively popular approach. However, this approach is laborious due to the immense quantity of experimental data and thus computer assistance would be of great assistance. To facilitate speed and accuracy of analysis, several automated systems have been developed.

Prior art systems have been designed to operate on images of electrophoresis gels in the form of digital images consisting of a matrix of values. There are at least two designs. One is based on a scanner to capture a gel image as a graphic file. Computer software is used to analyze the location of the bands and calculate the unknown molecular weight. The second design uses a digitizer, which requires users to point to bands using a pen. Again, software interprets these distances to calculate the molecular weights.

The scanner design (or densitometer) is expensive. Some scanner equipment are capable of capturing the bands directly from a gel placed on a UV box, while others involve digitizing a photographic image (a second generation reproduction, resulting in loss of image quality). As cameras have different sensitivities, faint bands may not be picked up by a scanner or by a pre-scanner camera (where a photo is scanned), which might otherwise be detected by the human eye.

Calculation of unknown molecular weights from gel analysis software uses an algorithm which identifies bands by contrasting dark/light spots with the background colour. The user must first assign the lane locations before the computer finds these "bands". Once the computer has marked the bands on the screen, the user must check to see if the computer has mistakenly identified an artifact as a band. This is a significant problem when the gel has a lot of background artifacts, or where the bands are not easily distinguishable from the background. Quite often there is no clear demarcation between the spot and its surrounding background using conventional boundary determination techniques. Consequently, when using a fully automated system, the researcher may be misled as to the results of the analysis since the system may erroneously utilize values which do not represent valid information about the desired spot to form a basis for generating its analytical output data. Thus, there exists a need for providing visual confirmation to the user as to the exact boundaries of the spot values that were used during the analysis.

Thus, there are many steps which require human assistance, including: scanning, assigning lanes (although some systems do this automatically), and checking whether artifacts have been mistaken for bands. Hence there are many steps involved in calculating the molecular weights. Scanners also take up a large amount of bench space, and the digitized images take up a lot of computer memory space.

In the second design, digitizing method, the user puts a picture/autoradiograph (not a gel) onto a tablet. The user then uses a pen or other device to point to bands on the picture. The position of the pen is then sent to a computer and interpreted by software, which performs the molecular weight calculations. Examples of this design of system are disclosed in U.S. Pat. No. 4,970,672 and U.S. Pat. No. 4,592,089.

This approach is expensive. It also suffers from lack of repeatability, as it is difficult to point to a band at exactly the same position every time. This is due to the fact that the operator relies only on human accuracy in two dimensional positioning.

Therefore, what is needed is an apparatus and methodology which is inexpensive yet overcomes the limitations of the devices known in the prior art.

SUMMARY OF THE INVENTION

The present invention relates to apparatus for measuring distances between a reference point and components of an image created by subjecting biological material to gel electrophoresis, comprising: a frame dimensioned to be adjustably positioned in a fixed location relative to an image, including a bar extending along a first axis; a carriage slideably coupled to the bar for movement along the first axis; alignment means extending transversely from the carriage along a second axis perpendicular to the first axis for aligning with a selected component of the image; and distance sensing means coupled to the carriage for sensing distance travelled by the carriage along the first axis and generating distance signals correlatable therewith.

The present invention is also directed towards a system for analyzing electrophoresis images, comprising measuring means for measuring distances between components of the image and processing means operatively coupled to the measuring means for processing the distance signals and generating maps based thereon. The measuring means comprises a frame dimensioned to be adjustably positioned in a fixed location relative to the image including a bar extending along a first axis, a carriage slideably coupled to the bar for movement along the first axis, alignment means extending transversely from the carriage along a second axis perpendicular to the first axis for aligning the carriage with a selected image, distance sensing means coupled to the carriage for sensing distance travelled by the carriage along the first axis and generating distance signals correlatable therewith.

The distance sensing means preferably includes input means for inputting current values of the distance signals to the processing means, such as a manually actuated switch located on the carriage. The distance sensing means preferably comprises a digital sensor which converts movement of the carriage into electrical signals which correlate with the distance travelled by the carriage. The processing means preferably comprises a computer system having memory means for storing the distance signals and mapping parameters, central processing unit having analyzing means for analyzing the distance signals, and mapping means for generating images.

A preferred embodiment of the invention is a system for constructing a restriction enzyme map from an image of bands created by subjecting DNA to gel electrophoresis. This system comprises measuring apparatus for measuring distances between a reference point and various bands of DNA, comprising a frame dimensioned to be adjustably positioned in a fixed location relative to the image including a bar extending along a first axis, a carriage slideably coupled to the bar for movement along the first axis, alignment means extending transversely from the carriage along a second axis perpendicular to the first axis for aligning the carriage with a selected image, distance sensing means operatively coupled to the carriage for measuring distance travelled by the carriage along the first axis and generating distance signals correlatable therewith, and processing means operatively coupled to the distance sensing means for processing the distance signals and generating maps based thereon.

BRIEF DESCRIPTION OF THE DRAWINGS

The present invention will now be described, by way of example only, with reference to the following drawings illustrating preferred embodiments of the invention, in which.

DETAILED DESCRIPTION THE A PREFERRED EMBODIMENTS

Figure 1:
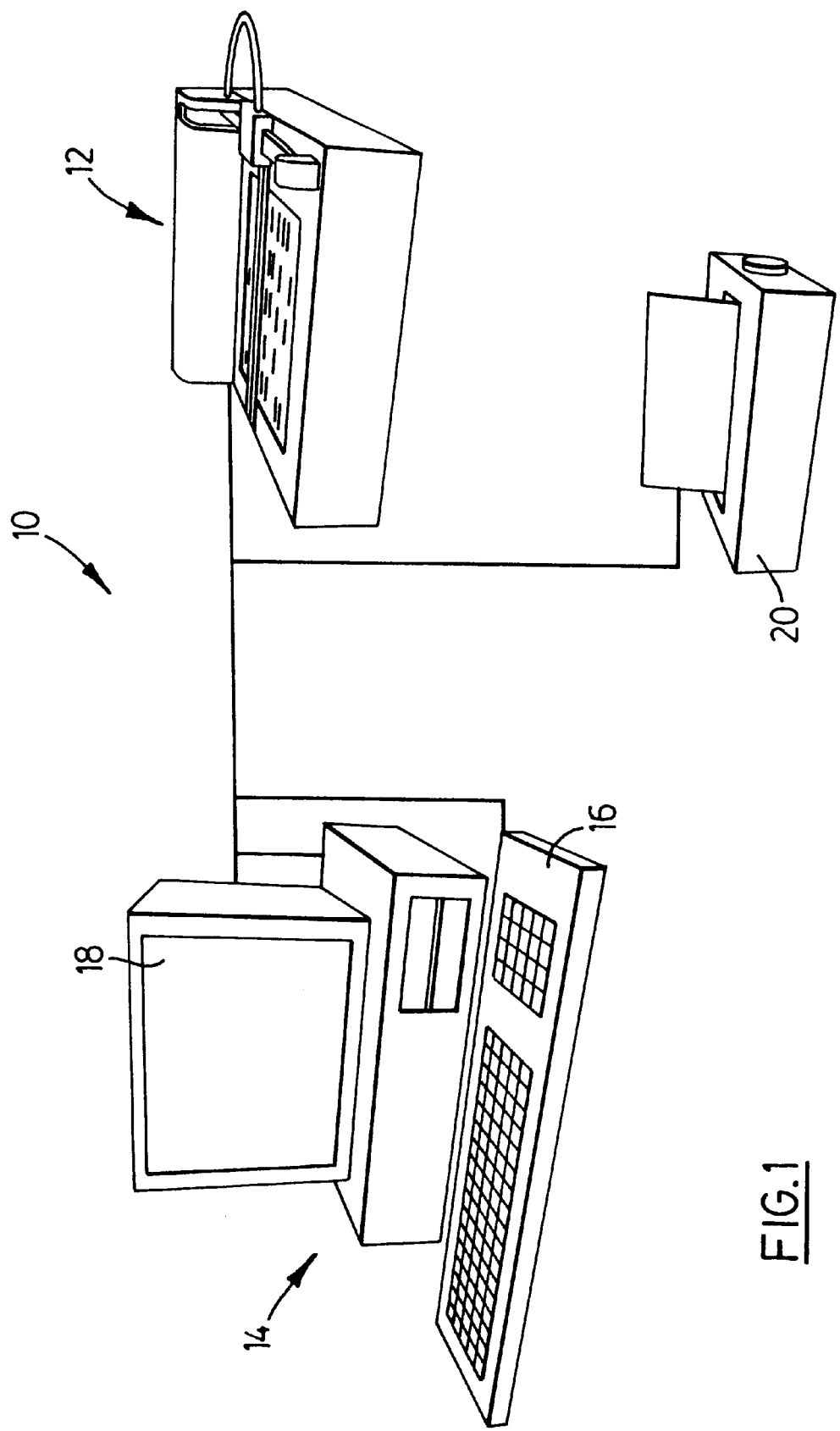
FIG. 1 is a perspective view of a preferred embodiment of the electrophoresis analysis system, made in accordance with the present invention.

Referring to FIG. 1, illustrated therein is a preferred embodiment of an electrophoresis analysis system 10 made in accordance with the present invention. Electrophoresis analysis system 10 comprises image measuring apparatus 12 electronically coupled to a computer 14 having a keyboard 16, monitor 18 and printer 20. Computer 14 includes a memory for storing the input signals and a central processing unit for processing the input signals received from measuring apparatus 12 and generating maps based on the analysis of the signals.

Figure 2:
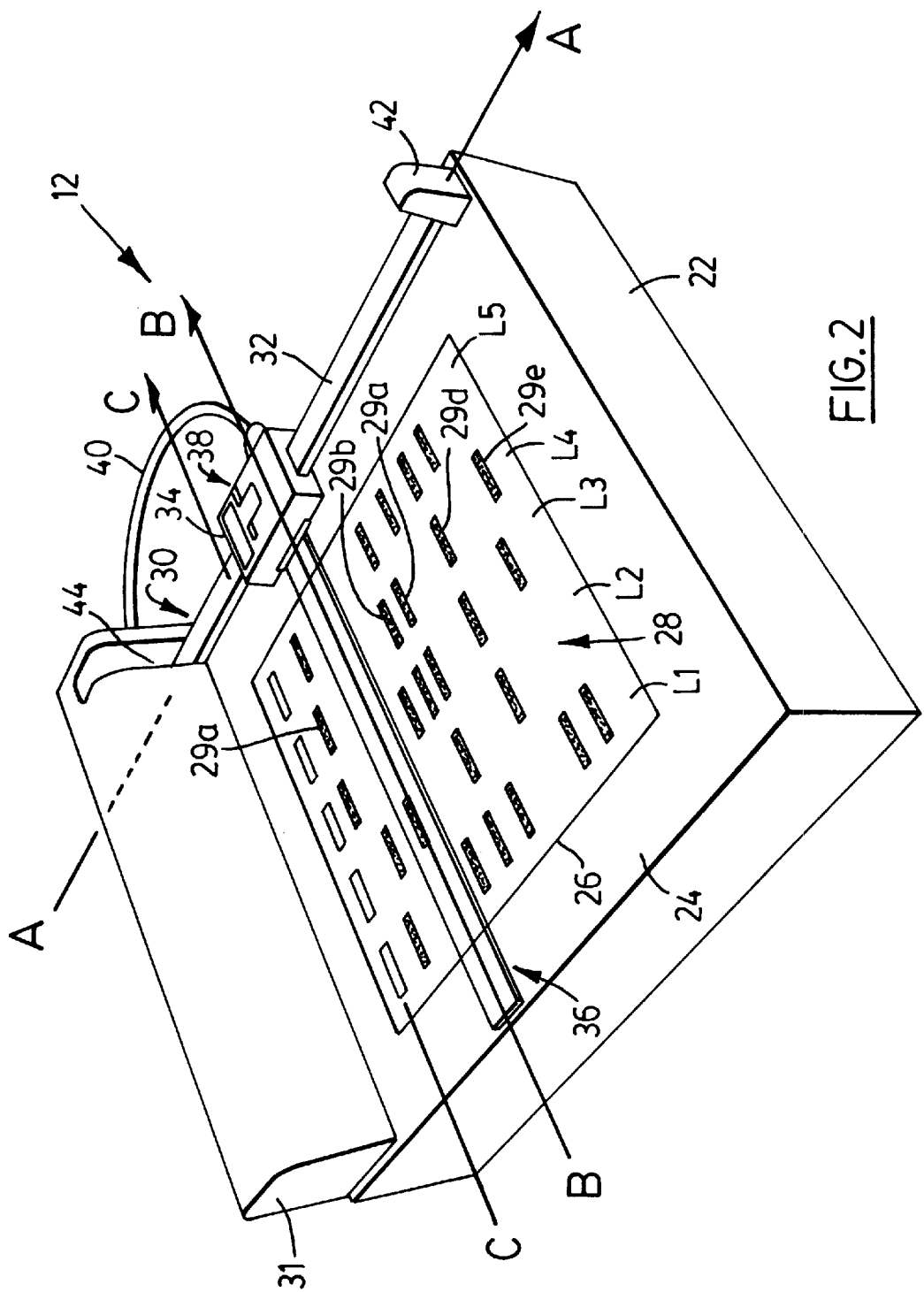
FIG. 2 is a front perspective view of a preferred embodiment of an electrophoresis image measuring apparatus made in accordance with the present invention, shown mounted on a light box.

Referring to FIG. 2, measuring apparatus 12 is shown mounted on a light box 22, having a flat top surface 24 on which is placed X-ray film 26 which displays an image 28 created by subjecting DNA to an electrophoresis gel. As shown, image 28 comprises a number of lanes L1, L2, L3, L4, and L5, each of which includes a series of bands or fragments. For example, lane L4 comprises a linear series of spaced DNA fragments or components 29a, 29b, 29c, 29d and 29e. Light box 22 has a transparent or translucent top surface 24 which allows light to pass through it from a light source within light box 22. As X-ray film 26 is translucent or transparent, light from light box 22 may pass through X-ray film 26 allowing image 28 to be more easily viewed by the operator.

Measuring apparatus 12 comprises a frame 30 which may be adjustably positioned to a fixed location relative to X-ray film 26, comprising a transverse frame portion 31 shaped to extend across the top of light box 22 and longitudinal bar 32 coupled to frame portion 31 and extending longitudinally along a first axis A. Bar 32 is preferably coupled to frame portion 31 by means of a hinge (not shown) at point 44, to allow bar 32 to be swung upwardly away from X-ray film 26. Bar 32 has a removably securably carriage stop 42 which prevents carriage 34 from being removed from the end of bar 32.

Measuring apparatus 12 also comprises carriage 34, distance sensor 38, and alignment means 36. Carriage 34 is shaped and dimensioned to slide freely on bar 32 along axis A while being substantially secured from movement along any other axis. Distance sensor 38 is housed in carriage 34, and generates distance signals correlatable with the distance travelled by carriage 34. Alignment means 36 is rigidly coupled to bar 32 so as to extend along an axis B, perpendicular to axis A. Cable 40 electronically couples distance sensor 38 to computer 14 via the computer's serial port.

Figure 3:
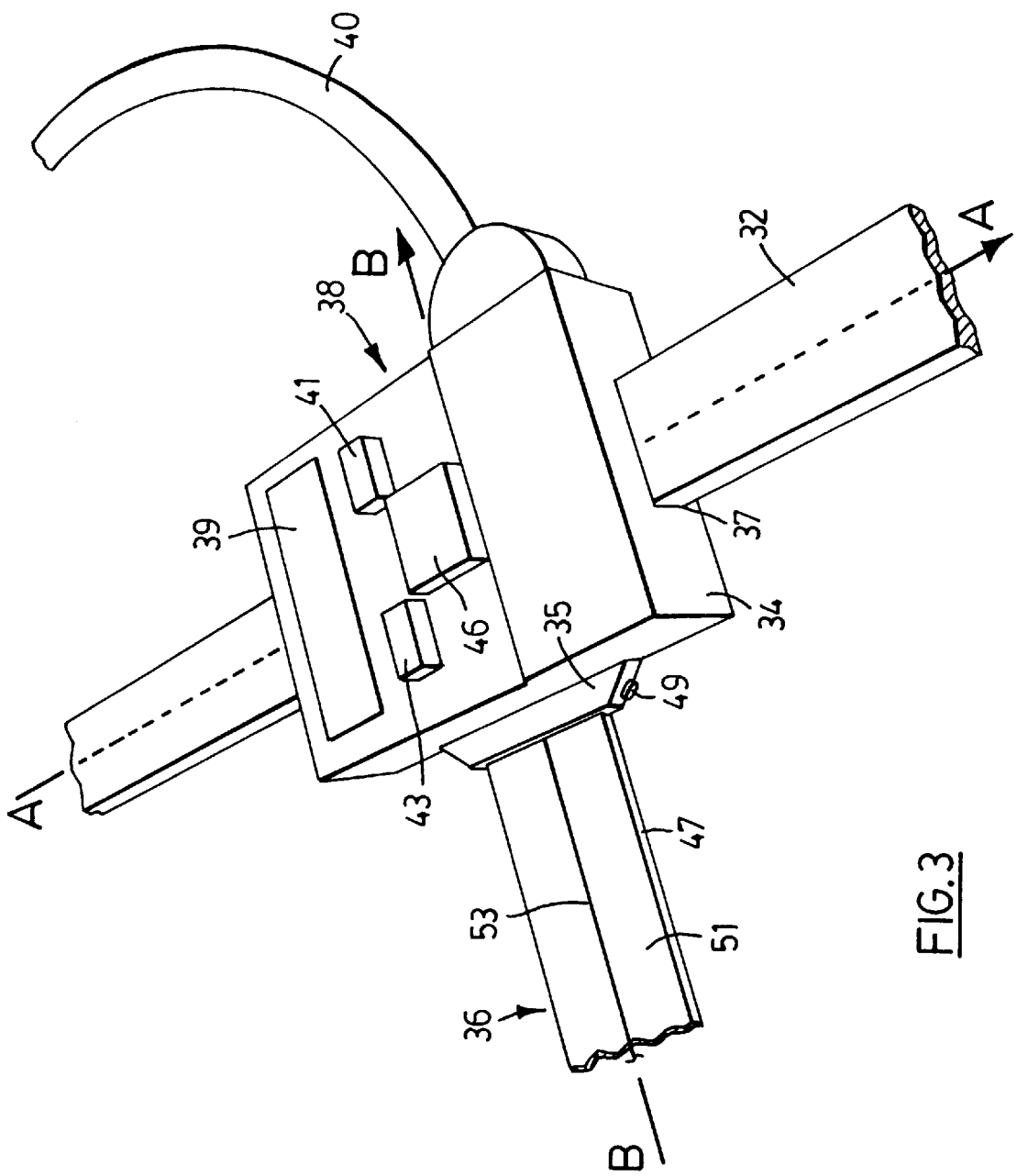
FIG. 3 is a detailed perspective view of a portion of the electrophoresis image measuring apparatus shown in FIG. 2.

Referring now to FIG. 3, distance sensor 38 is preferably a capacitive sensor such as a Fowler Sylvac™ sensor, having an LCD display 39, an off/reset button 41, a millimeters-to-inches conversion button 43. Distance sensor 38 also includes a manually actuatable input button 46 which activates sensor 38 and generates output distance signals which are sent to computer 14.

Alignment means 36 comprises an elongated ruler-like alignment bar 47 which is removably rigidly coupled to carriage 34 by coupling means 35. Alignment bar 47 has a transparent central viewing section 51 containing hairline 53 extending longitudinally along axis B. Coupling means 35 includes a slot shaped to receive alignment bar 47, and a retainer having release button 49, which releasably secures alignment bar 47 in the slot.

Figure 4C:
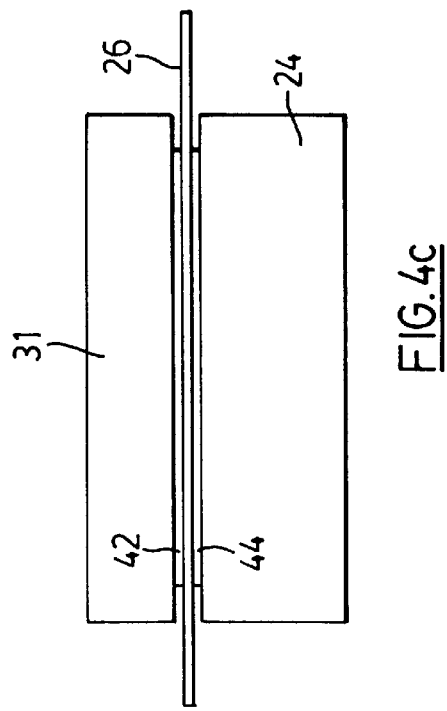
FIG. 4c is a schematic rear elevational view showing the frame housing mounted on the light box.
Figure 4A:
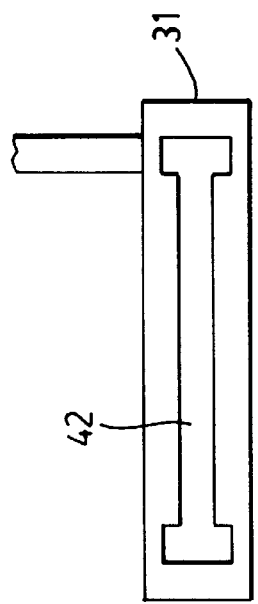
FIG. 4a is a schematic bottom plan view of the frame housing of the measuring apparatus of the subject invention.
Figure 4B:
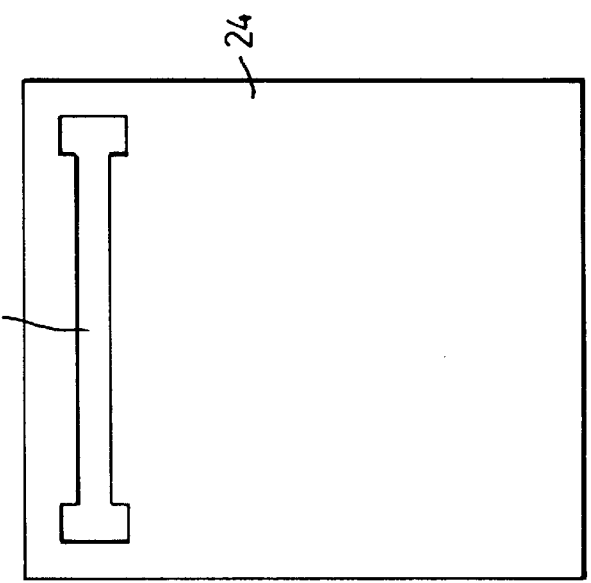
FIG. 4b is a schematic top plan view of a light box adapted for use with the measuring apparatus of the subject invention.

Referring now to FIGS. 4a–4c, frame 30 is preferably releasably secured to light box 22 by magnetic strip 42 on the bottom of transverse frame portion 31. Magnetic strip 42 is shaped to mate with a corresponding metallic or magnetic strip 44 on light box 24, sandwiching X-ray film 26 therebetween. Alternatively, frame 30 could include a clamp which can be used to lockably engage frame 30 to light box 22.

Figure 5:
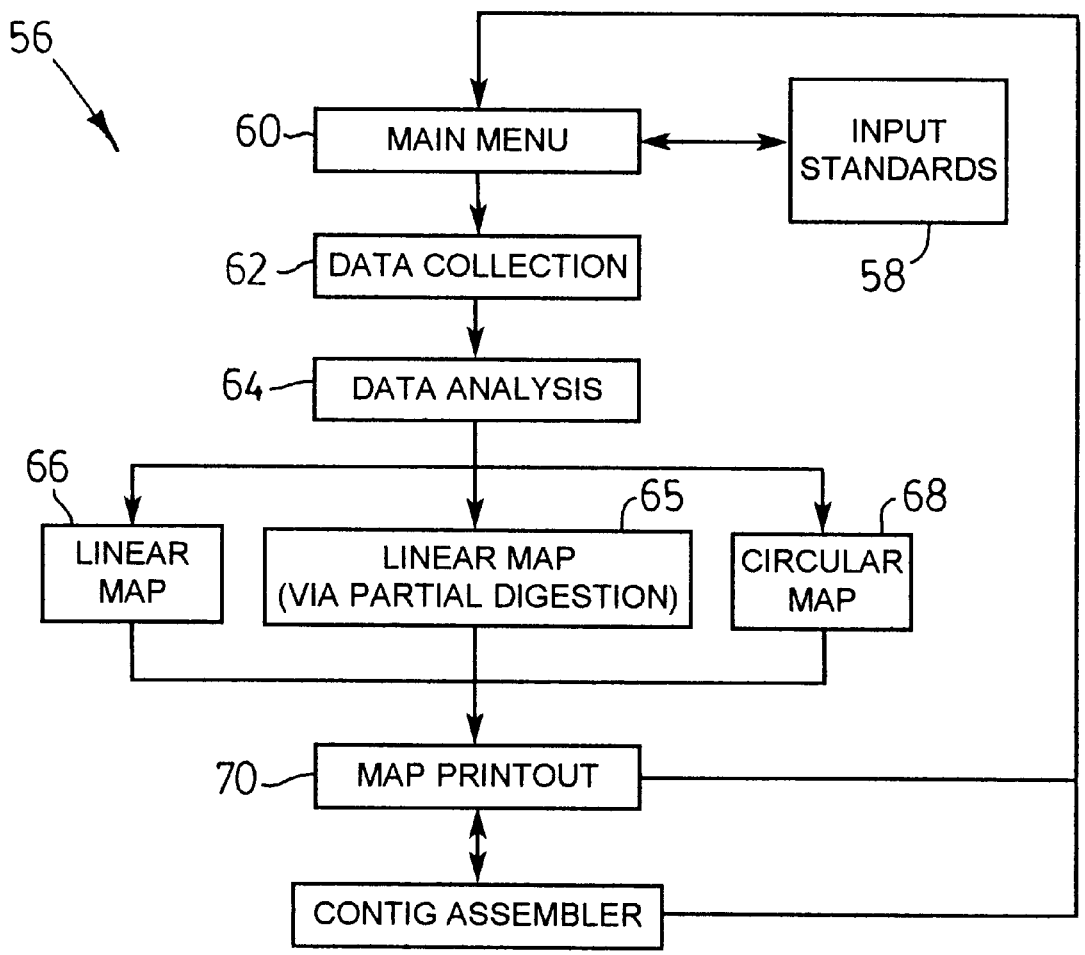
FIG. 5 is a flow chart illustrating the program flow of the processing means of the preferred embodiment.

Referring now to FIG. 5 and FIG. 1, computer 14 includes computer program 56 stored in memory which allows the central processing unit of computer 14 to analyze the distance signals from measuring apparatus 12. Program 56 includes user interface means for creating a main menu 60 which allows the operator to select the various operations of program 56, such as calibration, standards, data collection, and choice od data output. As shown in block 58, program 56 allows for measurement standards to be input through keyboard 16. Program 56 also includes a module for collection data corresponding to signals from distance sensor 38, (block 62) and a data analysis module (block 64), as applied by central processing unit 15, can then create a matrix of values corresponding to distances travelled by various components of images 28. This matrix may be stored in computer memory and further processed by data analysis module 64 to create maps or other output data based upon the processed distance signals and various mapping parameters.

Menu 60 allows an operator to select the form of output of the processed data, by using a partial digestion map module 65, a linear map module 66 or a circular map module 68. These modules create output map printouts 70 which graphically display the distances travelled by the individual components of image 28. The output data may then be used for further comparative analysis using the program as applied by central processing unit of computer 14. For example, maps generated by linear map module 66 can be compared for pattern similarities to construct contigs or composite maps encompassing a larger region of DNA.

In use, the subject system assists an operator in analyzing electrophoresis data. An X-ray film 26 is placed on vertical surface 24 of light box 22 and within frame 30 of measuring apparatus 12. An operator typically establishes a reference point along line C at the top of image 28, and then moves carriage 34 along bar 32 until a selected component of image 28 is aligned with hairline 53 of alignment means 36. As carriage 34 is moved along bar 32, distance sensor 38 measures the distance that carriage 34 travelled along bar 32. When the selected component of image 28 is aligned with alignment means 36, the operator actuates input button 46, which generates a distance signal which is transmitted through interface cable 40 to computer 14. Computer 14 stores the distance signal, and data analysis is carried out by program 56, as described above, to create maps or other output data.

An operator may input further information using keyboard 16. The information may pertain to, for example, the lane in which image 28 occurs, or any other information which may assist in analyzing the images 28. Central processing unit of computer 14 can then analyze the signals in relation to the signals from the measuring device, and generate output data, for example a map printout 70, based on the analysis of these signals by applying program 56 described above. Output maps 70 may be provided on monitor 18 printed by printer 20, or saved to a disk.

Hence, the invention combines the speed of computer 14, the accuracy of alignment means 36 coupled to bar 32, and the judgment of the experienced human eye. Identification of image 28 is not accomplished through a computer algorithm which may misidentify background smears as bands, but through an experienced human eye. Accuracy and repeatability is higher, because of the stability which bar 32 and frame 30 provide for the alignment means. Using the present invention, operator movement of the distance sensor is restricted to one axis. Thus, repeatability of each measurement is better than repeatability using instruments, such as pen-based digitizers, which operate in two-dimensions (i.e. that are not mechanically restrained to movement on one axis).

It will be seen by those in the art that, while the system of the invention is suitable for analyzing the images of an X-ray film, it is also suitable for analyzing a Polaroid picture or other photographic image of an electrophoresis gel or the like. In this use, the photograph of the electrophoresis gel is placed relative to frame 30 in the same or similar location as X-ray film 26 as shown in FIG. 1.

It should also be apparent that while preferred embodiment is adapted for DNA restriction enzyme mapping, the subject system can also be used to measure and analyze images of RNA and other proteins.

While the invention has been disclosed and described with reference to a limited number of embodiments, those skilled in the art will appreciate that the various modifications, variations and additions to the process is made, and it is therefore intended in the following claims to cover each such variation, addition and modification as falls within the true spirit and scope of the invention.

I claim:

1. Apparatus for measuring distances between a reference point and components of an image created by subjecting biological material to gel electrophoresis, comprising:

(a) a frame dimensioned to be adjustably positioned in a fixed location relative to an image, including a bar extending along a first axis;

(b) a carriage slideably coupled to the bar for manual movement along the first axis;

(c) an alignment device comprising a bar rigidly coupled to and extending transversely from the carriage along a second axis perpendicular to the first axis, enabling the operator to distinguish a selected component of the image and align the said bar therewith by manually moving the carriage along the first axis; and (d) a distance sensor coupled to the carriage for sensing distance travelled by the carriage along the first axis and generating distance signals correlatable therewith.

2. The apparatus as claimed in claim 1, wherein the alignment device comprises an elongated flat bar having a substantially transparent portion containing a longitudinally extending hair-line for viewing the components of the image.

3. The apparatus as claimed in claim 1, wherein the distance sensor comprises a digital sensor which converts movement of the carriage into digital electrical signals correlatable therewith.

4. The apparatus as claimed in claim 1, also comprising input means for inputting current values of the distance signals to a processing means, wherein the input means comprises a manually actuated switch located on the carriage and electronically coupled to the distance sensor.

5. A system for analyzing an image created by subjecting biological material to gel electrophoresis, comprising:
   (a) manual measuring means for measuring distances between components of the image, including:
      (i) a frame dimensioned to be adjustably positioned in a fixed location relative to the image, including a bar extending along a first axis;
      (ii) a carriage slideably coupled to the bar for manual movement along the first axis;
      (iii) an alignment device comprising a bar rigidly coupled to and extending transversely from the carriage along a second axis perpendicular to the first axis, enabling the operator to distinguish a selected component of the image and align the said bar therewith by manually moving the carriage along the first axis; and
      (iv) a distance sensor coupled to the carriage for sensing distance travelled by the carriage along the first axis and generating distance signals correlatable therewith; and
   (b) processing means operatively coupled to the measuring means for processing the distance signals and generating maps based thereon.

6. The system as claimed in claim 5, further comprising a support means for supporting the images on a flat two-dimensional surface.

7. The system as claimed in claim 6, wherein the frame comprises a magnetic strip for releasably securing the frame to the support means, and wherein the support means comprises a light source having a strip positioned and shaped to mate with the magnetic strip.

8. The system as claimed in claim 5, wherein the processing means comprises a computer having memory means for storing the distance signals and mapping parameters and analyzing means coupled to the memory means for analyzing the distance signals.

9. The system as claimed in claim 8, wherein the computer also comprises mapping means coupled to the analyzing means for creating the maps based upon the distance signals and mapping parameters.

10. A system for constructing a restriction enzyme map from an image of bands created by subjecting DNA to gel electrophoresis comprising:
   (a) measuring apparatus for measuring distances between a reference point and various bands of DNA, comprising:
      (i) a frame dimensioned to be adjustably positioned in a fixed location relative to the image, including a bar extending along a first axis;
      (ii) a carriage slideably coupled to the bar for manual movement along the first axis;
      (iii) an alignment device comprising a bar rigidly coupled to and extending transversely from the carriage along a second axis perpendicular to the first axis, enabling the operator to distinguish a selected component of the image and align the said bar therewith by manually moving the carriage along the first axis; and
      (iv) a distance sensor coupled to the carriage for sensing distance travelled by the carriage along the first axis and generating distance signals correlatable therewith; and
   (b) processing means operatively coupled to the distance sensor for processing the distance signals and generating maps based thereon.

11. The system defined in claim 10, wherein the alignment device comprises an elongated substantially transparent flat bar having a longitudinally extending hair-line for viewing the bands.

* * * * *